(12) United States Patent
Fraser et al.

(10) Patent No.: US 7,173,251 B2
(45) Date of Patent: Feb. 6, 2007

(54) DEVICES FOR IMAGING RADIONUCLIDE EMISSIONS

(75) Inventors: George William Fraser, Leicestershire (GB); Robert John Ott, Surrey (GB); John Ernest Wyper Lees, Leicester (GB)

(73) Assignee: University of Leicester, Leicestershire (GB)

( * ) Notice: Subject to any disclaimer, the term of this patent is extended or adjusted under 35 U.S.C. 154(b) by 291 days.

(21) Appl. No.: 10/433,799

(22) PCT Filed: Dec. 4, 2001

(86) PCT No.: PCT/GB01/05345

§ 371 (c)(1),
(2), (4) Date: Dec. 1, 2003

(87) PCT Pub. No.: WO02/46791

PCT Pub. Date: Jun. 13, 2002

(65) Prior Publication Data

US 2004/0079890 A1    Apr. 29, 2004

(30) Foreign Application Priority Data

Dec. 4, 2000    (GB)    ................... 0029430.6

(51) Int. Cl.
*G01T 1/24*    (2006.01)

(52) U.S. Cl. .................. 250/370.11; 378/98.8

(58) Field of Classification Search ........... 250/370.11, 250/370.09, 370.08, 332, 98.8, 98.12; 378/98.8, 378/98.12
See application file for complete search history.

(56) References Cited

U.S. PATENT DOCUMENTS

| | | | |
|---|---|---|---|
| 5,475,225 A | * | 12/1995 | Stettner .................. 250/370.11 |
| 6,031,892 A | | 2/2000 | Karellas |
| 6,445,767 B1 | * | 9/2002 | Karellas ..................... 378/98.8 |
| 6,895,077 B2 | * | 5/2005 | Karellas et al. ............ 378/98.3 |
| 2003/0169847 A1 | * | 9/2003 | Karellas et al. ............ 378/98.3 |

FOREIGN PATENT DOCUMENTS

| | | |
|---|---|---|
| GB | 2 343 577 | 5/2000 |
| WO | WO/97/16746 | 5/1997 |

OTHER PUBLICATIONS

Karellas, et al., "Imaging of Radionuclide Emissions with a Low-noise Charge-Coupled Device," *IEEE, Transactions on Nuclear Science*, vol. 40, No. 4, Aug. 1993, pp. 979-982.

* cited by examiner

*Primary Examiner*—David Porta
*Assistant Examiner*—Faye Boosalis
(74) *Attorney, Agent, or Firm*—Fredrikson & Byron, P.A.

(57) ABSTRACT

There is disclosed a device for imaging radionuclide emissions comprising: a charge coupled device or CMOS active pixel sensor device; and a scintillator layer in direct contact with the charge coupled device or CMOS active pixel sensor device; in which the thickness of the scintillator layer is greater than 200 μm, preferably greater than 400 μm, most preferably about 500 μm.

24 Claims, 2 Drawing Sheets

DEVICES FOR IMAGING RADIONUCLIDE EMISSIONS

This invention relates to devices for imaging radionuclide emissions.

Imaging of radiolabeled tracers in tissues (commonly referred to as autoradiography) has traditionally been performed using film to record the image. The use of film has the disadvantages of being time consuming, and having limited dynamic range and non-linear response. Furthermore, the technique is limited to the imaging of excised tissues.

A competing technology is known as a "gamma-camera", and comprises an array of small photomultiplier tubes equipped with a single crystal NaI scintillator. However, this device has the disadvantage of having a relatively limited intrinsic spatial resolution of ca. 3 to 4 mm. Furthermore, in practice the device requires a collimator in order to produce an image, which reduces the resolution to ca. 8 to 15 mm. Another competing technology utilises room temperature semiconductor arrays. However, such arrays are not routinely available and thus are expensive. Furthermore, the spatial resolution of the such arrays is no better than that obtained with gamma-cameras.

Karellas et al (IEEE Transactions on Nuclear Science, 40 (1993) 979) reports on imaging using charge coupled devices (CCDs) and a polycrystalline $Gd_2O_2S(Tb)$ scintillator. $Gd_2O_2S(Tb)$ is also known as "Gadox". Images were obtained using a lens to couple the Gadox scintillator to the CCD, i.e, the scintillator was physically separated from the CCD, although Karellas et al does suggest that either direct contact of the scintillator with the CCD or the use of a fibre optic reducer to couple the scintillator to the CCD may be possible. Karellas et al utilises relatively thin (<100 μm) layers of Gadox, and notes that problems of light absorption would be very significant if thicknesses of greater than about 200 μm are used. In other words, Karellas et al directs the skilled person towards the use of thin layers of Gadox. It is noted that Karellas et al does provide computations which suggest that an energy resolution ($\Delta E/E$) of between 0.08–0.10 might be achieved at an incident energy of 140 keV, but does not provide any indication of the experimental conditions needed to achieve this energy resolution.

CCDs which are directly coated with a thin (100 μm) layer of Gadox are known. Such devices have been extensively used in dental applications, specifically intra-oral X-ray imaging. However, such devices are only used for transmission imaging with low energy (25 to 40 keV) gamma rays and are unsuitable for imaging high energy gamma such as 140.5 keV gamma ray emission from $^{99m}Tc$.

The present invention overcomes the abovementioned problems and disadvantages, and provides a low cost, high performance device capable of imaging small volumes of radionuclide (such as $^{99m}Tc$) uptake in tissues. High performance with regard to spatial resolution and energy resolution is achieved. Furthermore, in-vivo imaging is possible.

According to a first aspect of the invention there is provided a device for imaging radionuclide emissions comprising:
- a charge coupled device or CMOS active pixel sensor device; and
- a scintillator layer in direct contact with the charge coupled device or CMOS active pixel sensor device;
- in which the thickness of the scintillator layer is greater than 200 μm, preferably greater than 400 μm, most preferably about 500 μm.

The use of a relatively thick layer of scintillator which is in direct contact with the CCD or CMOS active pixel sensor device enables high count rates, and allows excellent energy resolution to be achieved over the range 30–160 keV (although this range should not be considered to be a limiting one). This is surprising, particularly in view of Karellas et al which predicts that problems would be encountered if thick layers are used. Sub-millimetre spatial resolution is possible. Furthermore, the device is convenient and economic to produce.

The scintillator layer may comprise a rare earth phosphor, which may comprise Gd, and may comprise $Gd_2O_2S$ units. The rare earth phosphor may be $Gd_2O_2S(Tb)$ or $Gd_2O_2S$ (Pr, Ce, F).

The scintillator layer may comprise CsI.

The scintillator layer may be directly coated onto the device.

The device may further comprise a collimator. The collimator may be a coded aperture mask.

The device may further comprise means for operating the device in photon counting mode.

According to a second aspect of the invention there is provided an apparatus for imaging radionuclide emissions from a source, the apparatus comprising: a solid state pixel sensor device, a scintillator arranged between the source and the pixel sensor device, and a signal processing circuit coupled to receive an output from the pixel sensor device, which signal processing circuit is configurable to operate in a photon counting mode.

By operating in a photon counting mode the imager has an excellent energy resolution.

The apparatus may comprise a device according to the first aspect of the invention.

Devices in accordance with the invention will now be described with reference to the accompanying drawings, in which.

A standard CCD 10, for example a 684×456 array of 43 μm pixels, is coated with a 500 μm layer of Gadox 12. Coating methodologies are well known for the production of CCDs having a 100 μm thick layer of Gadox, and can be used to provide a 500 μm thick layer. A collimator 14 having a plurality of apertures 16 is disposed over the Gadox layer. The size of the apertures is the primary factor determining the spatial resolution of the device. Typically, collimators having apertures of ca. 500 μm diameter are utilised, but it is possible to use larger or smaller apertures as desired. The collimator may be fixed or detachable. In the latter case, it is possible to provide a single device having a number of associated collimators of different aperture size. In this way, the spatial resolution of the device can be varied as desired by the user. A coded aperture may be used. Such masks are well known to those skilled in the art, and permit three dimensional mapping of the radiolabeled area by image reconstruction. Such masks can have a random or a fixed pattern which might comprise an arrangement of circular, square or diagonal shaped apertures.

The device is operated by control means (not shown) which supplies power to the device and measures the output of the device. Preferably, the device is operated in photon counting mode. Cooling of the device, such as by Peltier cooling, is possible. Such operational techniques are well known to those skilled in the art.

With $^{99m}$Tc radionuclides (producing gamma rays of 140.5 keV energy), energy resolutions ΔE/E of 0.04 are possible, with a concomitant spatial resolution of 0.3–0.4 mm.

Figure 3:
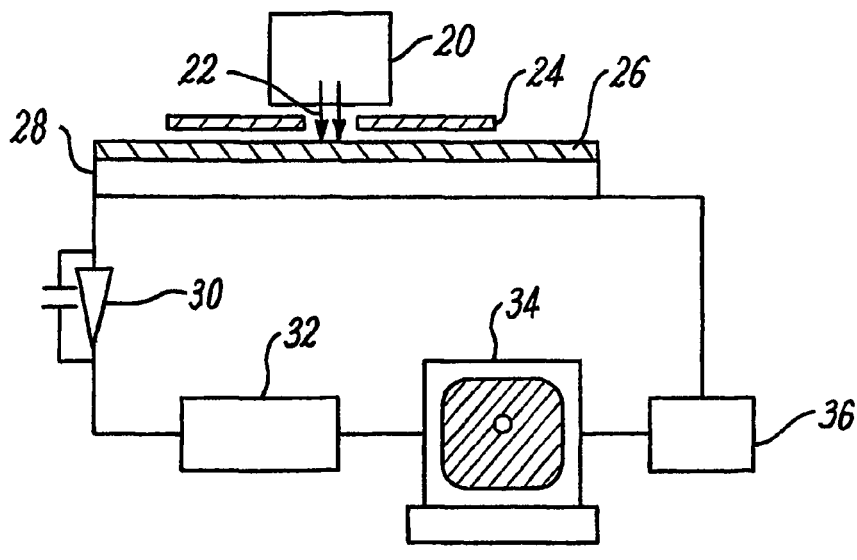
FIG. 3 shows a block diagram of an imaging apparatus in accordance with a further embodiment of the invention.

FIG. 3 shows a block diagram of an embodiment of an apparatus according to the present invention. The apparatus is shown in an experimental arrangement to determine the resolution of the apparatus but could equally provide an image of a radionuclide in vivo, for example.

A radionuclide source 20 comprises Americium 241 which emits gamma rays at an energy of 59.5 keV illustrated by the arrows 22. For the purposes of the resolution experiment these are applied to a lead sheet 24 having a pinhole in the centre which pinhole is 1 mm in diameter.

These gamma rays impinge upon a 500 micron layer of Gadox acting as a scintillator 26. The Gadox layer is formed on a charge coupled device (CCD) 28, specifically a Mtech CCD 38. The CCD and Gadox layer can be encapsulated in a suitable material, such as a plastic, in order, eg, to afford protection to the device. The CCD 28 is driven by drive electronics 36 and supplies an output to a signal processing circuitry 32 via low noise preamplifier 30. The drive electronics 36 are controlled at a high level by a personal computer (PC) 34 which also receives an output signal from the signal processing circuitry 32. An image of a spot (ie, the image of gamma rays travelling through the pinhole in the lead sheet 24) is shown on the screen of the PC 34. Replacing the Americium source and the lead sheet with a patient to whom a radioactive tracer has been administered provide an in vivo imaging function.

The signal processing circuitry 32 is configurable in a photon counting mode. This effectively means that the image from the CCD 28 is read sufficiently often to detect a single photon at a particular pixel location. The read rate required to accomplish this can be determined statistically. In this application the read rate will be 1 second or less.

While the Gadox layer is shown as being formed upon the CCD 28 it is possible to couple the photons produced in the scintillator layer to the CCD or other active pixel sensor device via a lens or via a fibre optic coupling. However, direct coupling is much preferred because of the substantially better efficiency in photon transfer compared with the other techniques. Preferably, the Gadox layer is at least 400 microns thick.

Although not explicitly shown in the diagram, cooling (for example Peltier cooling) is applied to the CCD 28. Without cooling the noise performance of the apparatus is degraded.

The CCD 28 could be replaced by a suitable CMOS active pixel sensor device.

Figure 1A:
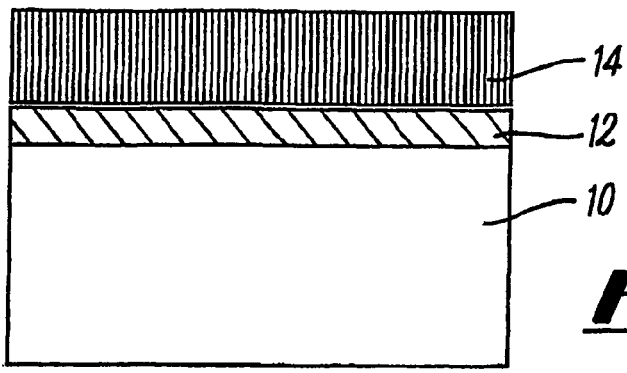
FIG. 1 shows a) a device according to the invention and b) a collimator.
Figure 1B:
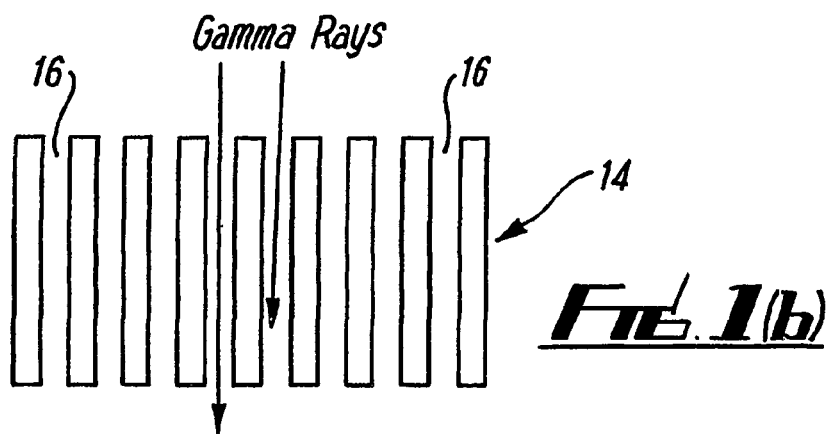
Figure 2A:
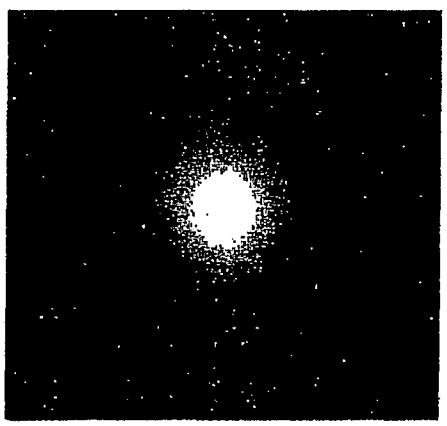
FIG. 2 shows (a) an image obtained by exposure of a device of the present invention to a $^{241}Am$ source and (b) a cross section through the spot image shown in (a)
Figure 2B:
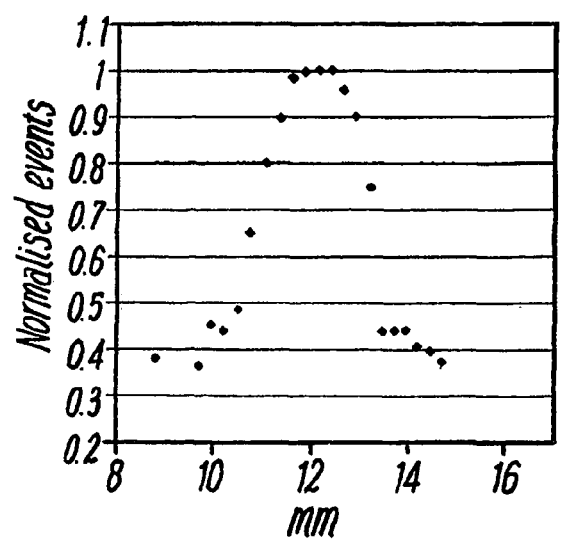

FIGS. 2(a) and 2(b) show an image from a $^{241}$Am source (59.5 keV). A CCD coated with a 500 μm layer of Gadox and having a 1 mm diameter pinhole disposed thereon was used to obtain the image. The cross section through the spot image shown in FIG. 2(b) indicates a spatial resolution of better than 0.7 mm. The derivation of this resolution will be explained with reference to FIG. 4.

Figures 4A, 4B:
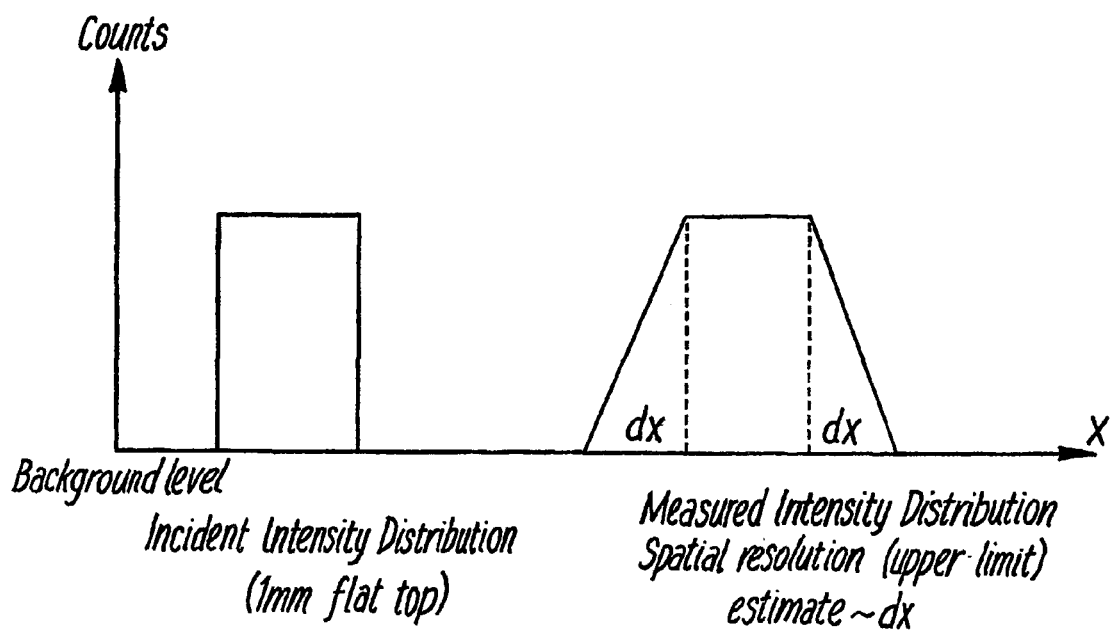
FIG. 4 shows (a) incident and (b) measured intensity distributions for the image of FIG. 3.

FIG. 4 illustrates the analysis of the results shown in FIG. 2 to determine the resolution of the arrangement in accordance with this embodiment of the invention shown in FIG. 3. FIG. 4 (a) shows the radiation incident upon the scintillator (and hence the CCD) as a consequence of the Americium source and the pinhole in the lead-a 1 mm wide 'flat top'. FIG. 4(b) shows a representation of the results of FIG. 2(b) ie, the measured intensity distribution.

The measured intensity distribution has spread on either side of the incident intensity distribution by an amount dx. This amount comprises the upper limit on spatial resolution (it should be noted that this comparatively crude technique provides an overestimate of the actual value). Comparison between FIG. 4(b) and FIG. 2(b), after substraction of the background intensity, shows that dx for this experiment is 0.7 mm.

In place of the CCD, it is possible to utilise a CMOS active pixel sensor device. Such devices are silicon devices which comprise, essentially, arrays of silicon diodes and associated transistors.

Detectors of the present invention, with sub-mm spatial resolution and excellent energy resolution over the range 30–160 keV, could be useful in detecting small breast cancers and tumours in lymph nodes and therefore may have considerable importance in treating breast cancer and in imaging melanoma and other small lesions.

The ability to image the 140.5 keV γ-ray emission from $^{99m}$Tc with high spatial resolution could be of benefit in other areas in nuclear medicine. These include single photon animal imaging to visualise radioactive tracers, particularly for the evaluation of new drugs, where there has been much work in developing high resolution PET scanners (R. Slates et al., 1999, "Design of small animal MR compatible PET scanner" IEEE Trans. Nucl. Sci. NS-46 565–570). Devices of the present invention could also provide a basis for an intra-operative probe for radio-guided cancer surgery. Mosaics of such detectors could be useful for the high resolution imaging of small organs such as the thyroid and skeletal joints (knees, ankles, elbows).

The invention claimed is:

1. A device for imaging radionuclide emissions comprising:
    a charge coupled device or CMOS active pixel sensor device; and
    a scintillator layer directly coated onto the charge coupled device or CMOS active pixel sensor device;
    in which the thickness of the scintillator layer is greater than 200 μm.
2. A device according to claim 1 in which the scintillator layer comprises a rare earth phosphor.
3. A device according to claim 2 in which the rare earth phosphor comprises Gd.
4. A device according to claim 3 in which the rare earth phosphor comprises $Gd_2O_2S$ units.
5. A device according to claim 4 in which the rare earth phosphor is $Gd_2O_2S(Tb)$.
6. A device according to claim 4 in which the rare earth phosphor is $Gd_2O_2S(Pr, Ce, F)$.
7. A device according to claim 1 in which the scintillator layer comprises CsI.
8. A device according to claim 1 further comprising a collimator.
9. A device according to claim 8 in which the collimator comprises a coded aperture mask.
10. A device according to claim 1 further comprising means for operating the device in photon counting mode.
11. A device according to claim 1, in which the thickness of the scintillator layer is greater than 400 μm.
12. A device according to claim 11 in which the scintillator layer comprises a rare earth phosphor.
13. A device according to claim 11 in which the scintillator layer comprises CsI.

14. A device according to claim 1, in which the thickness of the scintillator layer is about 500 μm.

15. A device according to claim 14 in which the scintillator layer comprises a rare earth phosphor.

16. A device according to claim 14 in which the scintillator layer comprises CsI.

17. An apparatus for imaging radionuclide emissions from a source, the apparatus comprising:
- a solid state pixel sensor device;
- a scintillator directly coated onto the pixel sensor device;
- a signal processing circuit coupled to receive an output from the pixel sensor device, which signal processing circuit is configurable to operate in a photon counting mode; and
- in which the thickness of the scintillator is greater than 200 μm.

18. An apparatus as claimed in claim 17, wherein the solid state pixel sensor device comprises a charge coupled device or a CMOS active pixel sensor device.

19. An apparatus as claimed in claim 17 wherein the signal processing circuit is configurable to operate in a photon counting mode by setting a read rate for the pixel sensor device less than a predetermined value.

20. An apparatus as claim in claim 19, wherein the predetermined value does not exceed 1 second.

21. An apparatus as claimed in claim 17, wherein the scintillator is at least 400 microns thick.

22. An apparatus as claimed in claim 17 further comprising cooling means for cooling the active pixel sensor.

23. An apparatus as claimed in claim 17 further comprising a coded aperture mask.

24. An apparatus according to claim 17 wherein the scintillator is about 500 μm thick.

* * * * *